United States Patent
Bocirnea

(10) Patent No.: US 8,417,043 B2
(45) Date of Patent: Apr. 9, 2013

(54) METHOD, APPARATUS AND COMPUTER PROGRAM PRODUCT FOR NORMALIZING AND PROCESSING MEDICAL IMAGES

(75) Inventor: Radu Catalin Bocirnea, New Westminster (CA)

(73) Assignee: McKesson Financial Holdings, Hamilton (BM)

( * ) Notice: Subject to any disclaimer, the term of this patent is extended or adjusted under 35 U.S.C. 154(b) by 107 days.

(21) Appl. No.: 13/075,495

(22) Filed: Mar. 30, 2011

(65) Prior Publication Data
US 2012/0250956 A1 Oct. 4, 2012

(51) Int. Cl.
*G06K 9/36* (2006.01)

(52) U.S. Cl.
USPC ........................................................ 382/235

(58) Field of Classification Search .................. 382/100, 382/128, 232–233; 709/203–207; 378/62; 128/920, 922, 923
See application file for complete search history.

(56) References Cited

U.S. PATENT DOCUMENTS

| | | | |
|---|---|---|---|
| 6,424,996 B1 * | 7/2002 | Killcommons et al. ...... | 709/206 |
| 6,633,674 B1 * | 10/2003 | Barnes et al. ................ | 382/232 |
| 6,912,317 B1 * | 6/2005 | Barnes et al. ................ | 382/239 |
| 6,937,767 B1 * | 8/2005 | Burak et al. .................. | 382/232 |
| 7,379,605 B1 * | 5/2008 | Ticsa ............................. | 382/232 |
| 7,489,825 B2 * | 2/2009 | Sirohey et al. ............... | 382/244 |
| 8,145,001 B2 * | 3/2012 | Khorasani et al. ........... | 382/232 |
| 8,145,006 B2 * | 3/2012 | Muto ............................ | 382/263 |
| 8,208,740 B2 * | 6/2012 | Thiagarajan ................. | 382/232 |

* cited by examiner

*Primary Examiner* — Jose Couso
(74) *Attorney, Agent, or Firm* — Alston & Bird LLP

(57) ABSTRACT

A method, apparatus and computer program product are provided to normalize DICOM image data such that normalized images may be efficiently transmitted to client devices and processed thereby. A method may include converting a DICOM image to a normalized image having a different file format, such as JPEG-XR format. The conversion of the DICOM image may include compressing the DICOM image and converting each of a plurality of pixels of the DICOM image to a grayscale pixel format and a color pixel format. The method may also create a set of related images having the different file format based upon the normalized image. The creation of the set of related images may include creating a plurality of images having different pixel dimensions that are smaller than the pixel dimensions of the normalized image. The method may also transform ancillary information related to the DICOM image to a human readable format.

30 Claims, 4 Drawing Sheets

METHOD, APPARATUS AND COMPUTER PROGRAM PRODUCT FOR NORMALIZING AND PROCESSING MEDICAL IMAGES

TECHNOLOGICAL FIELD

Embodiments of the present invention relate generally to the processing of medical images and, more particularly, to normalizing and processing medical images to facilitate transfer of the images to a client device.

BACKGROUND

Medical imaging often includes creating images of regions of the human body for clinical purposes, such as examination, diagnosis and/or treatment. These images may be acquired by a number of different imaging modalities including, for example, ultrasound (US), magnetic resonance (MR), positron emission tomography (PET), computed tomography (CT), mammograms (MG), digital radiology (DR), computed radiology (CR) or the like. In a number of example medical imaging workflows, such as in the case of a picture archiving and communications system (PACS), an image study for a patient may include one or more acquired images of the patient along with information that may reside with or otherwise accompany the images. This information may include, for example, a study identifier as well as patient information such as the patient's name, demographic information, medical record number or the like. The information may also include, for example, an indication of the modality that acquired the images of the study, the body region depicted in the images and/or the medical facility where the modality acquired the images. Once a patient study has been created, the study may be stored in the database of a central storage device. The images of the patient study may then be accessed and viewed via a dedicated viewer, such as a PACS workstation.

Medical images are frequently formatted in accordance with the digital imaging and communications in medicine (DICOM) standard. The DICOM standard generally requires the use of relatively complex code libraries. Additionally, the DICOM standard allows the utilization of a relatively large number of image compression algorithms and pixel representations. As a result, any viewer that is to process DICOM images must be configured to implement the complex algorithms that are necessary to interpret images formatted in accordance with the DICOM standard as well as all of the image de-compression algorithms allowed by the DICOM standard. Additionally, any viewer that is to process DICOM images must be able to properly interpret the plurality of different pixel representations allowed by the DICOM standard. As such, a viewer that is to process DICOM images may be quite complex.

As noted above, various algorithms may be utilized to compress DICOM images. As a result, the compressed images may not be manipulated in a consistent manner. For example, a server configured to process DICOM images may not consistently and in a computationally inexpensive manner supply rectangular sub-areas within an image to a viewer, as some of the compression techniques allowed by the DICOM standard do not provide effective techniques for extracting such sub-areas. Indeed, in some instances, the entire image would have to be decompressed, clipped and re-compressed in order to supply a rectangular sub-area, thereby resulting in a computationally expensive process.

DICOM images may be grouped in studies. Over the course of time, a patient may have undergone one or more medical examinations, thereby resulting in one or more studies. A medical imaging viewer generally displays information from one or more studies belonging to the same patient. However, the DICOM standard does not allow for an explicit definition of the logical structure of a study. Rather, a medical provider or other users of a medical imaging system must inspect every image of a study so as to deduce its logical structure, such as by determining the identifier that forms part of a DICOM image. In this regard, two images may be determined to belong to the same study if and only if the identifiers of the two images are identical. As a result, DICOM viewers are generally relatively slow to reveal the complete study structure to the user as the viewer is required to process each and every image in a study in order to determine the respective identifiers and, in turn, the study structure.

In order to define the logical structure of a study of DICOM images, servers have been developed to process the DICOM images and generate the logical structure of the images of a study. While the server is able to provide the DICOM images along with the logical structure of the DICOM images, the server also generates and stores a significant amount of meta-information that must also be provided to a viewer if the viewer is to present the study structure without having to parse each image in the study. Thus, the meta-information may refine or, in some instances, replace the DICOM structural information that was provided along with the study. This meta-information generally has a proprietary format that is readable only by complex specialized proprietary libraries. As such, viewers are required to have such proprietary libraries if the viewer is to make use of the meta-information. Such a specialized proprietary library generally is of a considerable size and complexity, thereby limiting its portability.

DICOM images may therefore be reviewed by dedicated DICOM viewers that are configured to process the images in accordance with the DICOM standard and, in some instances, in accordance with proprietary meta-information that is provided along with the DICOM images. As a result of the amount of data that must be transferred to the DICOM viewers in terms of image data and the associated meta-information as well as the complexity of the image processing required at such DICOM viewers, the viewing and processing of DICOM images is generally limited to dedicated viewers with limited, if any, portability.

BRIEF SUMMARY

The method, apparatus and computer program product of embodiments of the present invention are configured to normalize DICOM image data such that normalized images may be more efficiently transmitted and processed, thereby facilitating the review of normalized images that were generated from DICOM images on a wider variety of client devices. Thus, the methods, apparatus and computer program product of embodiments of the present invention permit client devices that are mobile and/or that are not dedicated to processing DICOM images to support the display of normalized images that were generated from DICOM images. Thus, the methods, apparatus and computer program product of embodiments of the present invention may provide more widespread access to normalized images that were created based upon DICOM images with less sophisticated client devices.

In one embodiment, a method of normalizing DICOM image data includes converting a DICOM image to a normalized image having a different file format, such as a JPEG-XR format. In this regard, the conversion of the DICOM image includes compressing the DICOM image and converting each of a plurality of pixels of the DICOM image to a grayscale pixel format and a color pixel format. The method of this embodiment also creates a set of related images having the different file format based upon the normalized image. The creation of the set of related images includes creating a plurality of images having different pixel dimensions that are smaller than the pixel dimensions of the normalized image. The method of this embodiment also transforms ancillary information related to the DICOM image to a human readable format.

The method of one embodiment may also create an image of a sub-area extracted from the normalized image without decompressing the normalized image. The method of one embodiment may also create one or more transformed images having the different file format based upon a normalized image. In this regard, the one or more transformed images may be created by flipping or rotating the normalized image. The method of one embodiment may also create one or more lower quality images based upon the normalized image without decompressing the normalized image.

In one embodiment, the transformation of the ancillary information includes storing the transformed information related to a grouping of images on a per-study basis and storing the transformed information related to a respective image in an image-specific manner. Transforming the ancillary information related to a respective image may include re-computing information related to image pixel values and to spatial position and orientation. The method of one embodiment may also include providing the normalized image to a client device via web services, such as via representational state transfer (REST) web services. Additionally, the method may include providing the ancillary information in a javascript object notation (JSON) format. The method may also include providing navigation information for a sequence of images in a study without providing individual image information. The navigation information may include navigational dimensions and boundaries for the navigational dimensions.

In another embodiment, an apparatus for normalizing DICOM image data is provided that includes processing circuitry configured to convert a DICOM image to a normalized image having a different file format, such as a JPEG-XR format, by compressing the DICOM image and converting each of a plurality of pixels of the DICOM image to a grayscale pixel format and a color pixel format. The processing circuitry may also be configured to create a set of related images having the different file format based upon the normalized image by creating a plurality of images having different pixel dimensions that are all smaller than the pixel dimensions of the normalized image. The processing circuitry may also be configured to transform ancillary information related to the DICOM image to a human readable format.

The processing circuitry may also be configured to create an image of a sub-area extracted from the normalized image without decompressing the normalized image. The processing circuitry may also be configured to create one or more transformed images having the different file format based upon the normalized image. In this regard, the transformed images may be created by flipping or rotating the normalized image. The processing circuitry may also be configured to create one or more lower quality images based upon the normalized image without decompressing the normalized image.

The processing circuitry of one embodiment is also configured to transform the ancillary information by storing the transformed information relating to a grouping of images on a per-study basis and storing the transformed information related to a respective image in an image-specific manner. In this regard, the processing circuitry may be configured to transform the ancillary information related to a respective image by re-computing information related to image pixel values and to spatial position and orientation. The processing circuitry of one embodiment may also be configured to provide the normalized image to a client device via web services, such as via REST web services. In this embodiment, the processing circuitry may also be configured to provide the ancillary information in a javascript object notation (JSON) format. The processing circuitry may also be configured to provide navigation information for a sequence of images in a study without providing individual image information. The navigation information includes navigational dimensions and boundaries for the navigational dimensions.

In a further embodiment, a computer program product for normalizing DICOM image data includes at least one computer-readable storage medium having computer-executable program code instructions stored therein. The computer-executable program code instructions include program code instructions for converting a DICOM image to a normalized image having a different file format, such as a JPEG-XR format. In this regard, the program code instructions for converting the DICOM image include program code instructions for compressing the DICOM image and converting each of a plurality of pixels of the DICOM image to a grayscale pixel format and a color pixel format. The program code instructions of this embodiment also include program code instructions for creating a set of related images having the different file format based upon the normalized image. The program code instructions for creating the set of related images include program code instructions for creating a plurality of images having different pixel dimensions that are smaller than the pixel dimensions of the normalized image. The program code instructions of this embodiment also include program code instructions for transforming ancillary information related to the DICOM image to a human readable format.

The computer program product of one embodiment may also include program code instructions for creating an image of a sub-area extracted from the normalized image without decompressing the normalized image. The computer program product of one embodiment may also include program code instructions for creating one or more transformed images having the different file format based upon a normalized image. In this regard, the one or more transformed images may be created by flipping or rotating the normalized image. The computer program product of one embodiment may also include program code instructions for creating one or more lower quality images based upon the normalized image without decompressing the normalized image.

In one embodiment, the program code instructions for transforming the ancillary information include program code instructions for storing the transformed information related to a grouping of images on a per-study basis and program code instructions for storing the transformed information related to a respective image in an image-specific manner. The program code instructions for transforming the ancillary information related to a respective image may include program code instructions for re-computing information related to image pixel values and to spatial position and orientation. The computer program product of one embodiment may also include program code instructions for providing the normalized image to a client device via web services, such as via representational state transfer (REST) web services. Additionally, the computer program product may include program code instructions for providing the ancillary information in a javascript object notation (JSON) format. The computer program product may also include program code instructions for providing navigation information for a sequence of images in a study without providing individual image information. The navigation information may include navigational dimensions and boundaries for the navigational dimensions.

BRIEF DESCRIPTION OF SEVERAL VIEWS OF THE DRAWINGS

Figure 1:
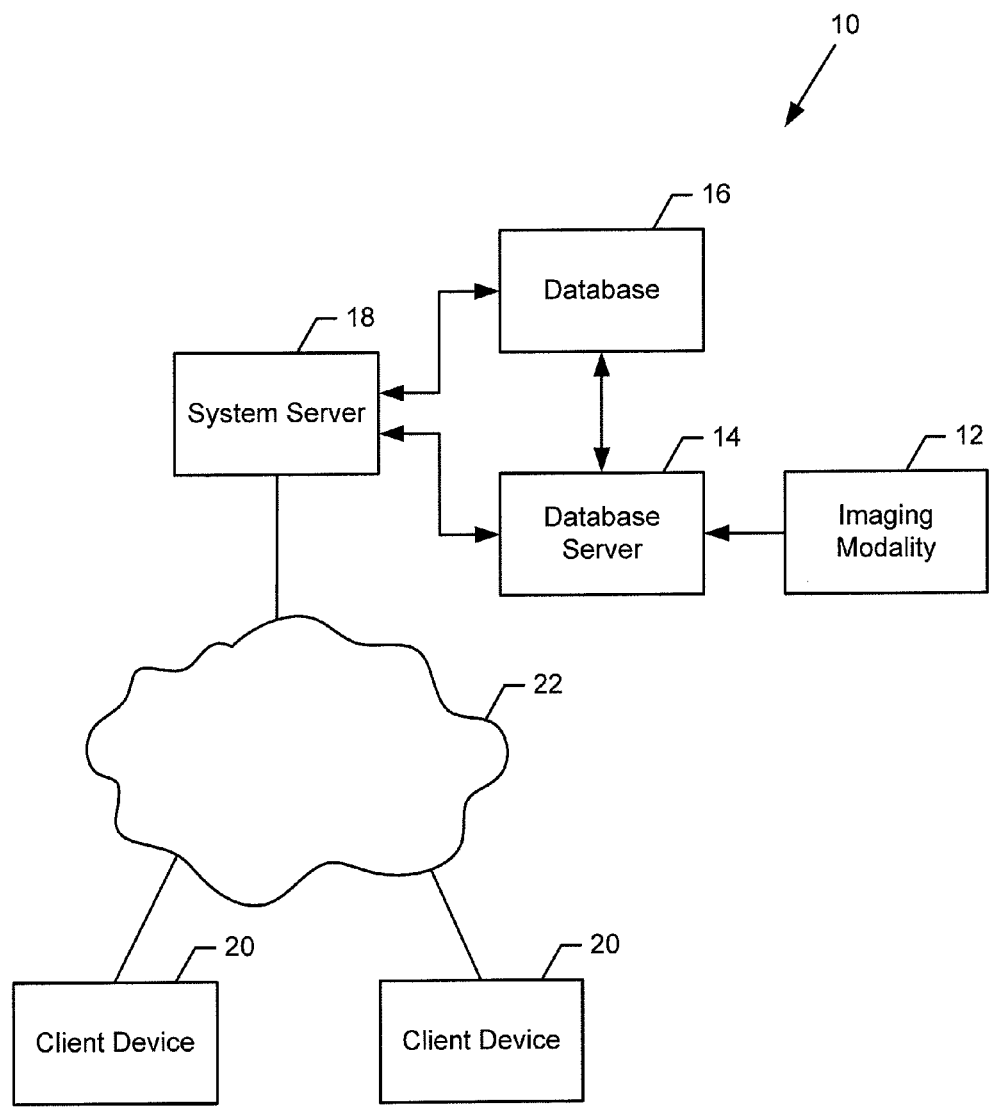
Figure 2:
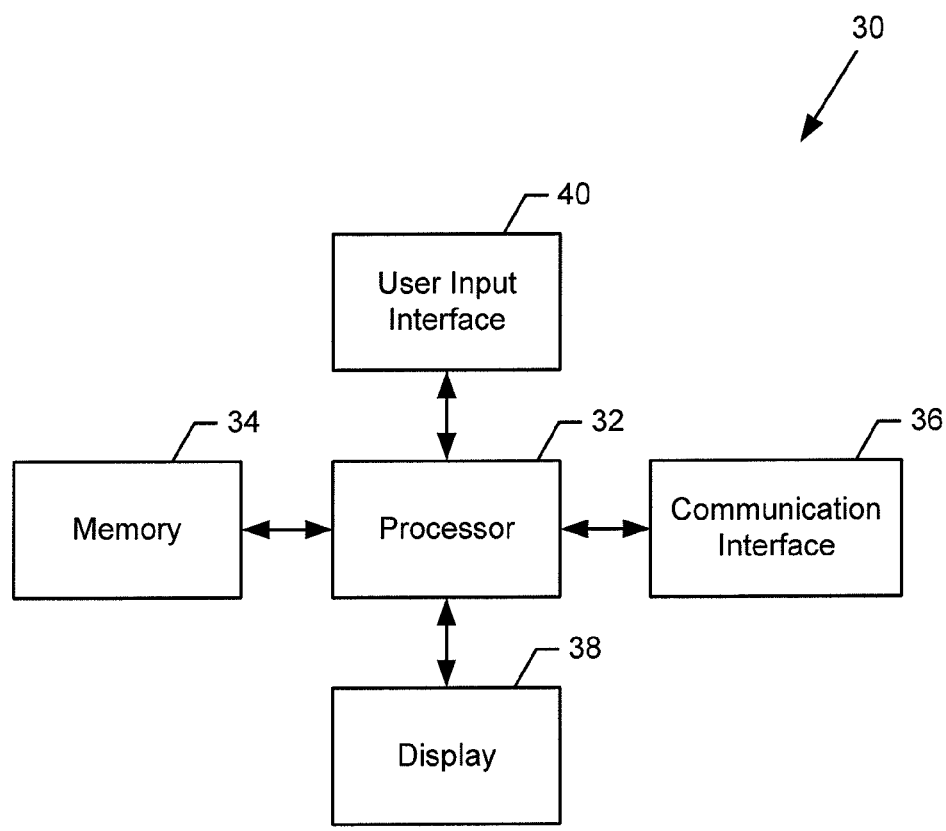
Figure 3:
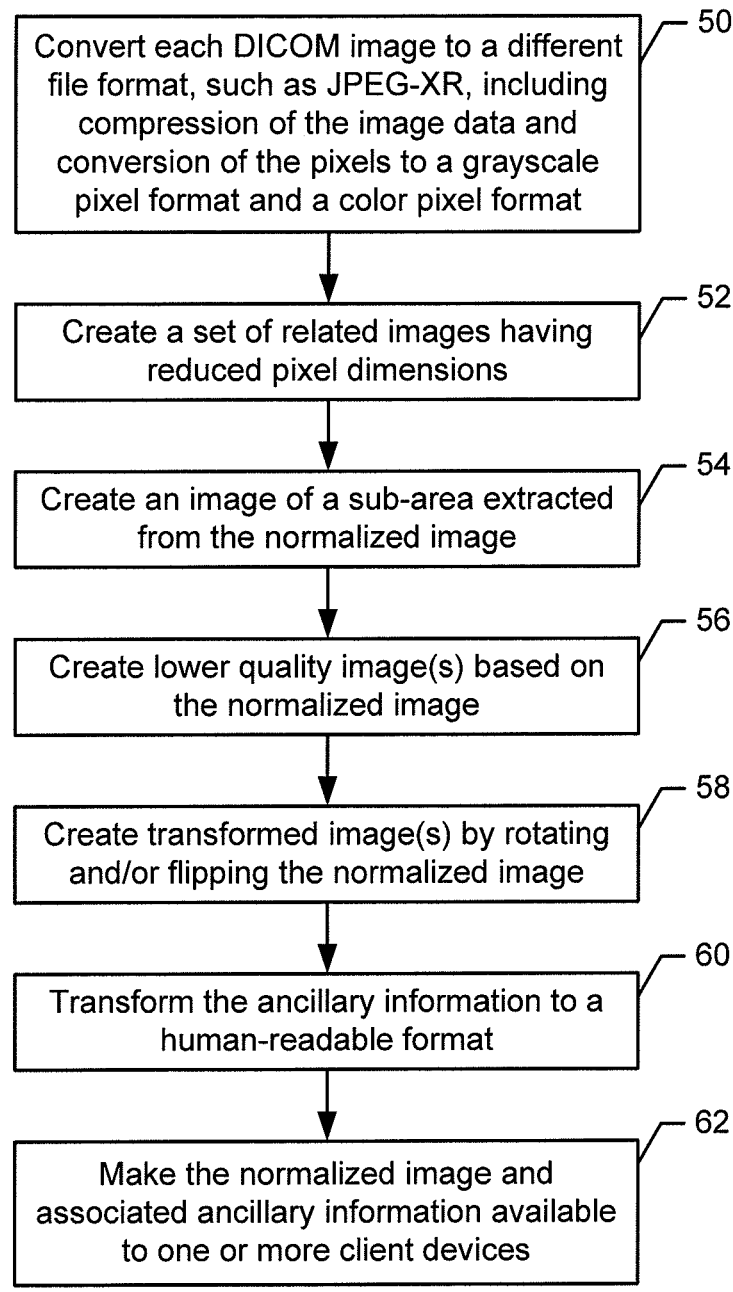
Figure 4:
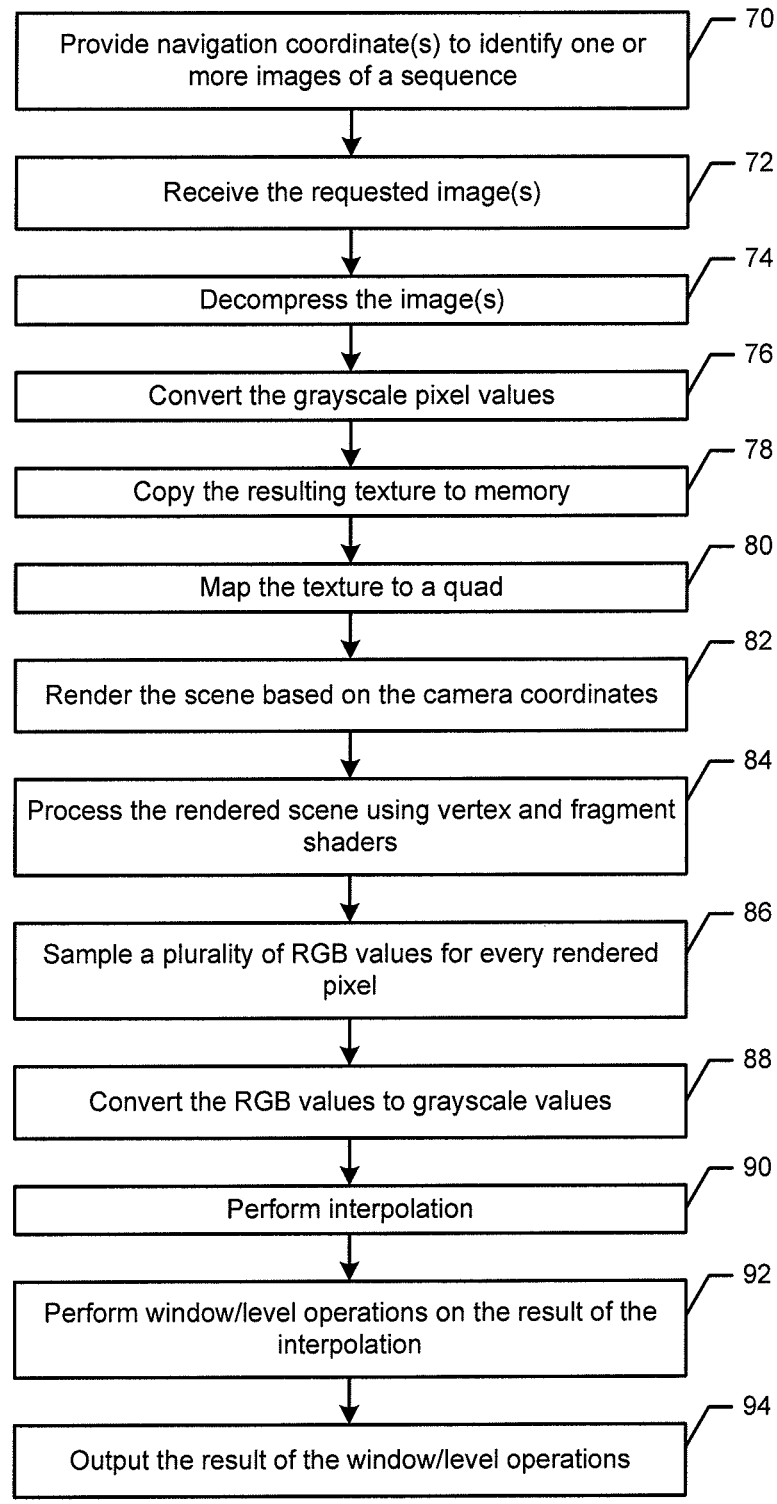

Having thus described embodiments of the invention in general terms, reference will now be made to the accompanying drawings, which are not necessarily drawn to scale, and wherein:

FIG. 1 is a schematic representation of a system in accordance with one embodiment to the present invention;

FIG. 2 is a block diagram of an apparatus that may be embodied as either a server or a client device in accordance with one embodiment of the present invention;

FIG. 3 is a flow chart illustrating operations performed by a server in accordance with one embodiment of the present invention; and FIG. 4 is a flow chart illustrating operations performed by a client device in accordance with one embodiment of the present invention.

DETAILED DESCRIPTION

The present invention now will be described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Further, the apparatus and method of example embodiments of the present invention will be primarily described in conjunction with medical-imaging applications. It should be understood, however, that the apparatus and method can be utilized in conjunction with a variety of other applications, both in the medical industry and outside of the medical industry. Like numbers refer to like elements throughout.

FIG. 1 illustrates a system 10 that may benefit from an example embodiment of the present invention. As shown, the system includes one or more imaging modalities 12 for acquiring an image, such as an image of the human body or parts of the human body for clinical purposes, such as examination, diagnosis and/or treatment. Examples of suitable modalities include, for example, ultrasound (US), magnetic resonance (MR), positron emission tomography (PET), computed tomography (CT), mammograms (MG) digital radiology (DR), computed radiology (CR) or the like.

The system 10 may also include one or more database servers 14 configured to receive image studies from the modalities 12 and other patient information such as patient text-based reports (e.g., unstructured, free-text reports), and archive the images and information in one or more databases 16 or other central storage devices. The database server and the database may be distinct from one another or the database server and the database may be logically separated, but co-located in another embodiment. In one example embodiment, the database server(s) and database(s) may form part of one or more of a hospital information system (HIS), radiology information system (RIS), picture archiving and communication system (PACS) or the like. The database server(s) may therefore include a HIS server, RIS server, PACS server or the like, each of which is configured to interface with a respective database. In other example embodiments, the database server(s) may include a database server configured to support multiple ones of a HIS, RIS and/or PACS server, logically separated but co-located within the respective server.

The system 10 may further include one or more servers providing one or more additional services to the database server 14 and/or client devices in communication with the system. As described below, these one or more servers may include a system server 18 for normalizing the images and for providing the normalized images as well as other ancillary information to client devices 20. In one embodiment, the database servers 14 may also function as the system server, while in another embodiment, the system server is distinct from the database server. As such, reference herein to a system server is intended to include any type of computing device, such as a database server, a dedicated server or the like, configured to perform the functions described herein in conjunction with the system server.

The imaging modality 12, database server 14, database 16 and/or system server 18 may be configured to directly and/or indirectly communicate with one another in any of a number of different manners including, for example, any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2 G, 2.5 G, 3 G or 4 G communication techniques, local area network (LAN), wireless LAN (WLAN) techniques or the like. In accordance with various ones of these techniques, the imaging modality, database server, database and/or system server may be coupled to and configured to communicate across one or more networks 22 to a client device 20. The network(s) may include any of a number of different combinations of one or more different types of networks, including data and/or voice networks. For example, the network(s) may include one or more data networks, such as a LAN, a metropolitan area network (MAN), and/or a wide area network (WAN) (e.g., Internet), and include one or more voice networks, such as a public-switched telephone network (PSTN). Although not shown, the network(s) may include one or more apparatuses such as one or more routers, switches or the like for relaying data, information or the like between the imaging modality, database server, database, system server and/or client device(s).

As shown in FIG. 1, the system server 18 is configured to communicate with one or more client devices 20, either directly or via a network 22. While the client device may comprise, include or be embodied in one or more fixed electronic devices, such as one or more of a desktop computer, workstation computer, server computer or the like, the client device may comprise, include or be embodied in one or more portable electronic devices, such as one or more of a mobile telephone, portable digital assistant (PDA), tablet computer, laptop computer, iPad® computer or the like. As such, the client device need not be a dedicated device, that is, a device dedicated to the processing and display of medical images, but may be a general purpose computing device in some embodiments.

Reference is now made to FIG. 2, which illustrates a block diagram of an apparatus 30 that may be configured to operate as or otherwise perform one or more functions of a system server 18 or a client device 20. The apparatus of exemplary embodiments of the present invention includes various means for performing one or more functions in accordance with example embodiments of the present invention, including those more particularly shown and described herein. It should be understood, however, that the apparatus may include alternative means for performing one or more like functions, without departing from the spirit and scope of the present invention.

As shown in FIG. 2, the apparatus 30 may include processing circuitry including, in one embodiment, a processor 32 that may include or otherwise be connected to a memory 34. The processor may be embodied in various forms. For example, the processor may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a special-purpose computer chip or the like. Regardless of its implementation, the processor may include or otherwise be associated with a graphical processing unit (GPU).

In an example embodiment, the processor 32 may be configured to execute instructions stored in the memory 34 or otherwise accessible to the processor. Alternatively or additionally, the processor may be configured to execute hard coded functionality. As such, whether configured by hardware or software methods, or by a combination thereof, the processor may represent an entity (e.g., physically embodied in circuitry) capable of performing operations according to an embodiment of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform the algorithms and/or operations described herein when the instructions are executed.

The memory 34 is tangible and non-transitory and may include volatile and/or non-volatile memory for storing content, data or the like. In this regard, the memory may store one or more software applications, modules, instructions or the like for the processor to perform steps associated with operation of the apparatus in accordance with embodiments of the present invention. The memory may also store content transmitted from, and/or received by, the apparatus 30. As described herein, the software application(s) may each comprise software operated by the apparatus. It should be understood, however, that any one or more of the software applications described herein may alternatively be implemented by firmware, hardware or any combination of software, firmware and/or hardware, without departing from the spirit and scope of the present invention.

In addition to the memory 34, the processor 32 may also be connected to at least one interface or other means for displaying, transmitting and/or receiving data, content or the like, such as in accordance with USB, RF, BT, IrDA, WLAN, LAN, MAN, WAN (e.g., Internet), PSTN techniques or the like. In this regard, the interface(s) may include at least one communication interface 36 or other means for transmitting and/or receiving data, content or the like. In addition to the communication interface(s), the interface(s) of the apparatus 30 embodied as a client device 20 may also include at least one user interface that may include one or more earphones and/or speakers, a display 38, and/or a user input interface 40. The user input interface, in turn, may include any of a number of devices allowing the apparatus to receive data from a user, such as a microphone, a keypad, a touch-sensitive surface (integral or separate from the display), a joystick, or other input device. In instances in which the apparatus is embodied as the system server 18, the apparatus need not include a user interface.

As indicated above, the client device 20 need not be dedicated to the viewing and processing of medical images and, as such, need not be, for example, a PACS workstation or viewer. Instead, the client device may be multipurpose computing devices, such as a mobile phone, PDA, iPad® computer or the like. While these types of client devices have some processing and memory capabilities and image processing functionality, these client devices may be more resource constrained than a conventional PACS workstation or other dedicated viewer. As such, the processing and memory required to decompress and view DICOM images may not be supported by some client devices, while other client devices may perform at least some of the decompressing and viewing functionality, but may require a substantial period of time to perform the decompression, thereby slowing the review process and potentially leading to dissatisfied users who are otherwise conditioned to relatively rapid data access. Accordingly, the system server 18 of an embodiment of the present invention may normalize the DICOM image and may otherwise perform substantial amounts of the image processing so as to reduce the image processing requirements of the client device, thereby permitting client devices that are not dedicated to an imaging system, such as PACS workstations, to receive and present images based upon DICOM images in a computationally efficient and timely manner so as to provide for an enhanced user experience.

As noted above, the medical images are generally formatted in accordance with the DICOM standard which allows the utilization of a large number of image compression algorithms and pixel representations. In order to facilitate the processing and display of images based upon the DICOM images by resource constrained client devices 20, the system server 18 may normalize the DICOM image data, thereby reducing the complexity of the image data that is provided to the client device by limiting representational variability and, in one embodiment, converting the data to consumer-grade standard formats that are supported by a wide variety of client devices. In order to normalize the DICOM image data, the processing circuitry of the system server may convert each of the DICOM images to respective normalized images having a different file format, such as a JPEG-XR format, as shown in block 50 of FIG. 3 which illustrates operations performed by the system server, such as the processing circuitry of the system server, in accordance with one embodiment. By converting the DICOM images to JPEG-XR images, for example, the system server compresses the image data, but avoids the issues associated with the allowance by the DICOM standard of a large number of different compression techniques, each of which must, in turn, be supported by the viewer by, instead, utilizing a limited number of compression techniques, such as a single compression technique, namely, the compression technique employed by JPEG-XR.

During the conversion of a DICOM image to a normalized image, the processing circuitry of the system server 18 may convert the plurality of pixels of each of the DICOM images to two formats, namely, a grayscale pixel format and a color pixel format. While various grayscale and color pixel formats may be utilized, the grayscale format may be an unsigned 16 bit grayscale format and the color pixel format may be an unsigned 24 bit color format. As such, the large number of pixel representations that are allowed by the DICOM standard and, as such, were required to be supported by viewers of DICOM images may similarly be simplified so as to require the support of only two formats, that is, a grayscale pixel format and a color pixel format, by a client device 20. Accordingly, the complexity of the client device may be materially reduced as a result of the reduction in the number of compression algorithms and pixel formats that must be supported with the client device. Indeed, the client device may only require a single codec for decompression and need only implement two distinct image processing algorithms for displaying and manipulating the image buffer based upon the two pixel representations. As a result of the conversion of the DICOM image to a normalized image, the client device also need not implement DICOM parsing so as to decompress and display the image and, as such, need not include a DICOM stack.

In addition to converting each DICOM image to a normalized image having a different file format, such as a JPEG-XR format, the system server 18, such as the processing circuitry, may also create a set of related images having the different file format, such as the JPEG-XR format, based upon the normalized image. See block 52 of FIG. 3. In this regard, the set of related images may include a plurality of images having different pixel dimensions that are all smaller than the pixel dimensions of a normalized image, even though all of the images within the set depict the same image information. By creating a plurality of images that each has different pixel dimensions, typically in advance of any request form the client device 20 for the image, the system server may thereafter provide a client device 20 with an image having pixel dimensions that correspond to the display supported by the client device. Accordingly, the client device may receive an image that may be readily processed and displayed by the client device and will not require much, if any, further processing in order to further reduce the size of the image.

Although the number of images in the set and the dimensions of the images in the set may be varied, the creation of one example set of images having a reduced size is described below for purposes of illustration. In this embodiment, the DICOM image may have X number of pixels in a row and Y number of pixels in a column. Additionally, the set of related images created by the system server 18 may be designated $\{I_1 \ldots I_n\}$. As described above, the system server may create an initial normalized image, designated $I_0$, which has the same pixel dimensions as the original image, that is, X×Y. In this embodiment, $\{I_1 \ldots I_n\}$ may have monotonic decreasing pixel dimensions. For example, in an instance in which $D_n$ represents the dimensions of image $I_n$, the set of images may be defined as $\{I_1 \ldots I_n; D_n = \{X/(2_n), Y/(2_n)\}$ and $(X/2_n \geq 2_k$ or $Y/2_n \geq 2_k)\}$ In this representation, the maximum dimension of the smallest image in the set is $2^k$. Although the maximum dimensions of the smallest image may be defined to be any of a wide variety of sizes, the maximum dimensions of the smallest image are generally driven by the display requirements of the client devices to which the images will be served. In one example, k=7 such that the maximum dimension of the smallest image in the set is no smaller than 128 (or $2^7$).

In addition to creating a set of related images having smaller pixel dimensions than the normalized image, the system server 18, such as the processing circuitry, of one embodiment may also create a number of other images based upon the normalized image that may be provided to the client device 20, such as upon request in order to limit the processing required by the client device and to facilitate the display of a variety of representations of the normalized image in a computationally efficient and timely manner. Advantageously, the processing circuitry of the system server of one embodiment may permit the related images to be created based upon the compressed representation of the normalized image without requiring the decompression of the normalized image, thereby facilitating the creation of the related images and reducing the computational requirements associated with the creation of a set of related images.

As shown in block 54 of FIG. 3, for example, the system server 18, such as the processing circuitry, may create an image of a sub-area extracted from the normalized image without decompressing the normalized image. Although the sub-area may have various dimensions and shapes, the system server of one embodiment may create an image of a rectangular sub-area extracted from the normalized image. In one embodiment, the system server may create the image of a sub-area in response to a request by a client device 20, as opposed to persistently storing the image of the sub-area in advance of a request by the client device.

Alternatively or additionally, the processing circuitry of the system server 18 may create one or more lower quality images based upon the normalized image (and relative to the quality of the normalized image) without decompressing the normalized image. See block 56 of FIG. 3. As such, the quality of the image served to a client device 20 may be readily tailored to the requirements of the client device, thereby allowing the client device to be provided with an image having a quality that is supported by the client device without requiring the client device to perform substantial image processing. In one embodiment, the system server may create the lower quality image(s) in response to a request by a client device 20.

The processing circuitry of the system server 18 may also create one or more transformed images having the different file format, such as a JPEG-XR format, based upon the normalized image. As shown in block 58 of FIG. 3, the transformed images may be created by flipping the normalized image, such as about either a vertical or a horizontal axis, and/or by rotating the normalized image by a predefined angular amount, such as 90°, 180°, 270° or the like. As described above, the transformation of the normalized image may be accomplished in a compressed domain such that the normalized image need not be decompressed in order to create the transformed images, thereby reducing the computational complexity required of the system server. By creating the transformed image at the system server, the transformed images may be provided, typically upon request, to the client device 20 for viewing without requiring substantial, if any, image processing by the client device, thereby further simplifying the design and requirements of the client device. In order to facilitate the provision of transformed images to the client device, the system server may generate the transformed images in advance of a request from the client device. The transformed images may be of particular import in the medical industry since medical images, such as DICOM images, are generally displayed in certain clinically dictated orientations, some of which involve flipping or rotating the initial image, such that the creation of the transformed images by the system server facilitates the review of the images based upon the DICOM images in the various clinically-dictated orientations in an efficient manner.

In addition to the DICOM images, an image study and/or the individual images of an image study may be associated with ancillary information that is typically provided in a proprietary manner or in accordance with the DICOM standard. In this regard, ancillary information may include, but is not limited to, information associated with (including being derived from) a DICOM image or other DICOM element of a study other than the image pixel data. The ancillary information may also include information derived from an interpretation of the pixel values of one or more DICOM images such as, for example, information used in the computer-aided diagnosis (CAD) regarding tumor detection. This ancillary information may take many different forms, but may include information relating to image grouping, image presentation and annotations. In accordance with one embodiment of the present invention, the system server 18, such as the processing circuitry of the system server, transforms the ancillary information related to the DICOM image to a human-readable format. See block 60 of FIG. 3. In this regard, the information pertaining to an image study, such as relating to the study structure, e.g., the grouping of images, may be stored and provided on a per-study basis, such as in a per-study extensible markup language (XML) blob. Alternatively or additionally, information specific to a respective image may be stored in an image-specific manner, such as in an image-specific XML blob.

During the transformation of the ancillary information, the system server 18, such as the processing circuitry, may re-compute some of the information such that the information is correlated with the image pixel format of the normalized image. By way of example, the medical meaning of image pixel values, such as density, etc., may be re-computed during the transformation of the ancillary information so as to match the pixel format of the normalized image since the conversion of an image from one pixel format, such as the DICOM format, to another format, such as a JPEG-XR format, may change the effective values of the image pixels even though no information is lost in the conversion. By way of another example, the ancillary information related to the spatial position and orientation of the image may be re-computed during the transformation of the ancillary information such that the transformed ancillary information correlates to or matches the spatial position and orientation of the image following the transformation. Accordingly, the ancillary information is intended to convey the same information following transformation, although the ancillary information may need to be re-computed, as described above in some instances in order to take into account changes in the normalized image or the images related to the normalized image relative to the original DICOM image.

The system server 18, such as the processing circuitry, may transform the ancillary information into a variety of different human-readable formats. As noted above, the ancillary information may be transformed to an XML format. Alternatively, the ancillary information may be transformed to a JSON format. In one embodiment, the human-readable format to which the ancillary information is transformed is one that is supported by a wide variety of client devices 20 and may be readily parsed by the client devices.

Once the DICOM image and the associated ancillary information have been converted and transformed, respectively, the normalized image as well as any related images and the associated ancillary information may be made available to the client devices 20. In one embodiment, the system server 18, such as the processing circuitry and/or the communication interface 36, is configured to provide the normalized image to the client device via web services, such as web services over hypertext transfer protocol (HTTP) or HTTP secure (HTTPS). The method and apparatus may employ different types of web services, such as simple object access protocol (SOAP). However, in one embodiment, the system server is configured to provide the normalized image and the transformed ancillary data to the client device via representational state transfer (REST) web services. Similarly, the system server may provide the transformed ancillary information in a variety of different formats. In one embodiment, however, the transformed ancillary information is provided to the client device in a JSON format to facilitate access to and use of this information on a wide variety of client platforms.

As described above, the medical images have been normalized and the resulting normalized images, such as in a JPEG-XR format, are provided by the system server 18 to the client devices 20. The normalized images, such as the JPEG-XR images, may retain the high dynamic range of the original DICOM images with no loss of information. As such, a client device functioning as an image viewer may advantageously perform image processing operations, such as windows/level operations, kernel operations, etc., internally and without requiring round trip communications with the system server. This capability to perform the image processing operations at the client device without round trip communication with the system server is relevant in that the frame rate is therefore only dependent upon the processing power of the client device and not upon the network latency. As such, the interactive image manipulation experience of a user may be improved, oftentimes in a relatively dramatic manner, with no image quality degradation, no network utilization (therefore reducing network load) and no lag, which is especially relevant for network configurations having a relatively high latency.

As described above, the system server 18 may also provide a number of other images related to the normalized image, such as images having smaller sizes, images of sub-areas, images having lower quality and/or transformed images. The availability and provision of these related images by the system server facilitate the display of such images by the client devices 20 without extensive image processing resources or time being expended by the client devices.

Additionally, the transformed ancillary information as provided from the system server 18 to a client device 20 may provide immediate access to any selected image(s) of a study or other set of images. In this regard, the ancillary information may include structural study information, that is, information on the clinically-relevant components of the study, and may be provided to the client device without requiring the client device to receive and process each of the images of the study. Thus, the client device may select the image that is of most relevance and may obtain the respective image without having to receive and process all of the other images of the study, thereby reducing network traffic and increasing the efficiency with which the respective image may be served and viewed. The structural study information may include definitions of the ordered sets, also known as sequences, of related study elements, such as an ordered collection of images or other clinical entities associated with the study, such as reports, scanned documents, etc. The structural study information may also include relevant details of the sequences, such as the type of the sequences, e.g., volume, cine-clip, key images, reports, scanned documents, etc. As a result of the transformation of the ancillary information, the information may be immediately available, may be extensible in terms of both supported types and contents, and served in accordance with a human-readable standard, such as JSON, XML or the like.

In terms of the immediate availability, the system server 18, such as the processing circuitry, may compute or otherwise determine, for each sequence, a representative visual depiction of the sequence. This visual depiction may be pre-computed and/or cached and may include images and/or textual information and/or overlays depicting the sequence. As such, the graphical representation of each sequence that is determined by the system server may be immediately available to the client device 20, such as for determining the image(s) to be requested from the system server. Further details regarding the visual depiction are provided by a U.S. patent application entitled Apparatus, Method and Computer Readable Storage Mediums for Browsing and Selecting a Multimedia Object filed concurrently herewith, the contents of which are incorporated herein by reference.

The ancillary information provided for each sequence in the study may be such as to allow a user to navigate to an arbitrary location in the sequence and may be provided by the system server 18, such as the processing circuitry and/or the communication interface 36, to the client device 20 in advance of the images. The ancillary information for a sequence of images within a study may include the sequence type, a sequence identifier that is unique with respect at least to the study, and navigation information specific to the sequence type. However, the navigation information that facilitates navigation amongst the images does not include actual image information. Instead, the navigation information may include the dimensions along which navigation can be performed.

These dimensions may include, but are not limited to, time, space, e.g., position and orientation in patient space, a set of numbers, such as a set of positive natural numbers, for example, to define the navigation through a set of ordered elements, etc. The navigation information may also include boundaries defining the limits within which navigation is allowed over the specified dimensions. The boundaries may include temporal boundaries associated with time-based dimensions, such as the duration of a cine-clip consisting of a sequence of images, spatial boundaries for space-based dimensions, such as the extent of a volume in space for a set of images representing a three-dimensional volume, ordinal boundaries, such as the number of elements in an ordered set of elements, both temporal and spatial dimensions, such as for a four-dimensional volume consisting of a three-dimensional volume evolving in time, phase based navigation, etc. The navigation information may also include the orientation and patient space shared by all of the images that comprise a three-dimensional volume, the frame duration of the frames in a cine-clip which may be a constant value, etc. Additionally, the navigation information may associate text, graphical elements and/or other explanatory and/or labeling information with one or all of the navigation dimensions, thereby supporting an extensible set of navigation dimensions. This type of navigation information may convey the meaning, nature and intent of the navigation dimension(s) to the user and/or may configure the behavior of the client device 20.

By defining the ancillary information to include the navigation information and by providing such information to the client devices 20 in advance of any individual image information, the system server 18, such as the processing circuitry, may provide the client devices with the ancillary information including the navigation information in a relatively quick manner and without requiring the transfer of the images of an image sequence or even a listing of the images of the image sequence or any information specific to the individual images. In this regard, the size of the ancillary information, such as navigational information, is not dependent upon the size of a study or sequence, such as in terms of the number of elements. As such, the ancillary information, such as navigation information, may be provided in advance for a relatively large study or sequence in order to permit the client device to select the images of interest from within the relatively large study or sequence. However, the ancillary information, such as navigation information, provided initially may remain relatively small in size, even though the study or sequence is large. Since the number of images of an image sequence may be significant, such as hundreds or thousands or tens of thousands of images, the provision of the navigation information and other ancillary information in advance of image information can improve the transport and processing performance of the system as provision of the image information including the unique identifiers of the images which may be of significant size may otherwise lead to transport or processing performance issues. Indeed, efforts to include image-specific ancillary information may abruptly increase the processing, transmission and memory overhead.

In generating the navigation information, the system server 18, such as the processing circuitry, may provide different navigational information for different types of sequences. With respect to a cine-clip, it may be advantageous to be able to navigate to a certain moment in time. As such, the system server may provide navigational information that includes time-based dimensions to facilitate navigation to a specific moment of time within the cine-clip. Accordingly, the navigation information may identify the cine-clip sequence and may provide a time value for navigational purposes. As another example, navigation within a three-dimensional volume may rely upon position, orientation and potentially the thickness of the slab or other workpiece. As such, the system server may provide navigational information that includes boundaries for the images within the sequence based upon position, orientation and thickness. Still further, navigation through an ordered set of images, reports, scanned documents, etc., may be based upon the number of images in the ordered set. As such, the system server may provide navigational information for this type of sequence that defines an index, such as in terms of a set of positive natural numbers.

In order to obtain an image from a respective sequence, the client device 20, such as the processing circuitry and/or the communication interface 36, may provide one or more navigation coordinates to the system server 18 based upon the boundaries associated with the respective sequence. See block 70 of FIG. 4, which illustrates operations that may be performed by the client device. In this regard, the number and type of supplied coordinates depends upon the number and type of dimensions along which intra-sequence navigation may be performed. The values of these coordinates should fall within the respective sequence boundaries. Upon receipt of a set of navigational coordinates, the system server, such as the processing circuitry and/or the communication interface, may provide one of the images that has been previously generated and stored by the system server or one or more images that are rendered by the system server in response to the request by the client device. The client device generally does not take into consideration whether the image has already been generated or must be rendered by the system server, thereby reducing the complexity of the client device by reducing the computational requirements of the client device.

As described, the system server 18 may have created, normalized and stored a number of images in advance of a request from a client device 20. In one embodiment, however, the system server may also render one or more images in response to a request from a client device in an instance in which the system server has not previously stored the requested image. For example, the system server may render an image in an instance in which the navigation coordinates point to an existing DICOM image, but the system server has not yet created the normalized version of the image. The system server may also render an image in an instance in which the navigation coordinates specify an entity that represents a combination of existing DICOM images. For example, the navigation coordinates could specify a spatial slab that has a spatial location, dimensions and/or orientation that encompasses sections of one or more existing DICOM images, such as in a multi-planar reconstruction (MPR) scenario. Still further, the system server may render an image in an instance in which the navigation coordinates encompass dimensions other than the ones described above, such as, for example, dimensions requiring advanced image processing that would be disadvantageous to offload to the client device. For example, such advanced image processing may include image segmentation in which relevant areas of the image are specifically identified and either excluded from display or processed in a specific manner. More generally, navigation dimensions, as used herein, may extend beyond spatial and temporal aspects and may, instead, reference different views or representations of a particular image or a particular group of mages. As such, the representation requested by a client device may not physically exist on the system server and would need to be rendered, such as on the fly.

Along with the image, the system server, such as the processing device and/or the communication interface, may provide meta-information. The meta-information may be the product of a prior transformation of ancillary information (and, as such, may be stored along with or otherwise in associated with a previously stored image) or may be dynamically generated in response to the request from the client device, such as in the instance of an image that is rendered by the system server in response to a request from the client device.

By receiving the navigation information in advance of individual image information, a client device 20 can determine the particular images or groups of images that would be of interest and may then issue a request to the system server 18 for those images. The system server may, in turn, provide the requested images in such a manner that a client device can subsequently display the images without substantial further processing. By providing only the requested images, however, the amount of information transferred from the system server to the client device is managed so as to reduce the transmission and bandwidth requirements of the system.

As indicated above, the client device 20 may be a multi-purpose device, such as a laptop computer, mobile telephone, PDA or the like. For example, the client device of one embodiment may be an iPad®-based viewer. However, a system 10 implementing the method and apparatus of embodiments of the present invention may permit the client device to achieve near-instantaneous access to arbitrary images and reports within arbitrary studies. In this regard, the client device may receive the ancillary information including the navigation information and may identify, based upon the navigation information, the image(s) within a respective sequence of a study that would be of interest. The client device may then submit a request for the respective images and may, in turn, receive the images that have been previously generated and stored or that are dynamically rendered by the system server 18. See blocks 70 and 72 of FIG. 4. In either instance, the client device, such as the processing circuitry, may then present the images upon the display 38 and permit user interaction with the images, such as via the user input interface 40.

In one embodiment, the client device 20 includes means, such as the processing circuitry, for decompressing the images received from the system server 18. See block 74 of FIG. 4. Even though the images may be representative of DICOM images, which permits a wide number of compression algorithms to be utilized, the method and apparatus of one embodiment may allow the use of a limited number of compression algorithms, such as only a single compression algorithm, e.g., the compression algorithm utilized by JPEG-XR. As such, the client device can readily decompress the images received from the system server. During the decompression, the client device may readily process the pixel values that have a color format utilizing the various channels of a multi-channel output buffer of the processor 32, such as the red (R), green (G) and blue (B) channels of an RGB output buffer or the R, G, B and transparency (A) channels of an RGBA output buffer. For example, pixel values having a 24 bit color format or a 24 bit grayscale format may be readily processed utilizing the R, G and B channels, each of which includes 8 bits for a total of 24 bits. Additionally, pixel values having a 32 bit grayscale format may be processed utilizing the R, G, B and A channels of an RGBA output buffer. However, the client device, such as the processing circuitry, may convert the pixel values that have a grayscale format during the decompression process. See block 76 of FIG. 4. By converting the pixel values having a grayscale format as described below, the client device may advantageously avoid the creation of two image buffers that would require copying data therebetween at the time of conversion and would correspondingly reduce the image conversion performance of the client device.

In this embodiment, a client device 20, such as the processing circuitry, may convert a 16 bit grayscale image by mapping a 16 bit grayscale pixel value into two channels of the RGB output buffer, such as the red and the green channels of the RGB or RGBA output buffer, although any two of the channels may be utilized. As such, each channel includes fewer bits than the 16 bit grayscale pixel value. For example, each channel may include 8 bits with the 8 most significant bits being mapped, for example, to one channel, and the 8 least significant bits being mapped to another channel. In one embodiment in which the 16 bit grayscale value is represented as X, X may be represented as X=R+256*G such that the 8 most significant bits are mapped to the G channel, and the 8 least significant bits are mapped to the R channel. In one embodiment, the client device, such as the processing circuitry, can map the 16 bit grayscale values in this manner by employing memory copy operations, as opposed to mathematical manipulation of the 16 bit value representing the grayscale image, thereby further improving the image processing efficiency. Additionally, while an embodiment employing a 16 bit pixel value is described above, the method and apparatus of embodiments of the present invention may convert pixel values having other sizes.

The client device 20, such as the processing circuitry, may set the texture width and height to the lowest powers of 2 that are larger than the width and height of the decompressed image, respectively. In this regard, the useful area, that is, the area occupied by actual image information, of the resulting texture may be smaller than the actual texture size. By defining the texture width and height in this manner, however, the client device can maintain relatively good rendering performance even in an instance in which the client device is computationally constrained in such a manner as not to perform well with textures that have dimensions other than with powers of 2.

Following the decompression, the client device 18, such as the processing circuitry, may copy the resulting texture to memory 34, such as the memory associated with a graphical processing unit of the processor 32. See block 78 of FIG. 4. The client device, such as the processing circuitry, may also map the texture to a quad, that is, a set of two triangles forming a rectangle. See block 80. The dimensions of the quad may be such that the aspect ratio of the original image is maintained. The client device, such as the processing circuitry, may then render the scene based upon the camera coordinates so that the desired image zoom and rotation are achieved. See block 82. The client device, such as the processing circuitry, may then further process the image, such as by utilizing vertex and/or fragment shaders. See block 84. As will be understood, a vertex shader performs vertex-oriented operations, that is, the vertex shading program is run for every rendered vertex, such as the corners of a quad. As will also be understood, a fragment or pixel shader performs per-pixel operations, that is, the fragment shading program is run for every rendered pixel.

In one embodiment, the client device 20, such as the processing circuitry, e.g., the GPU, implementing the pixel shader may sample a plurality of RGB values, such as 4 RGB values, for every rendered pixel. See block 86. While this sampling may be performed in various manners, the processing circuitry of the client device of one embodiment may be configured to sample the RGB values utilizing a nearest-neighbor algorithm. The client device, such as the processing circuitry, may then convert the plurality of RGB values back to respective grayscale values, e.g., 16 bit grayscale values, such as by performing the inverse of the operations described above in conjunction with the conversion or mapping of the 16 bit grayscale image values to two 8 bit channels of the RGB output buffer. See block 88. Based upon the resulting 16 bit grayscale value, the client device, such as the processing circuitry, may perform an interpolation, such as a bilinear interpolation, bicubic interpolation or the like, on the plurality of grayscale values. See block 90. The client device, such as the processing circuitry, may then perform window/level operations on the result of the interpolation and may provide the result of the window/level operation as an output, such as for display. See blocks 92 and 94. The client device may be configured to perform various window/level operations including a linear window/level operation based on parameters determined by the client device based on meta-information received by the client device and supplied to the processing circuitry, such as the GPU. Alternatively, the client device may be configured to implement other window-level operations including, for example, those employing a polynomial transfer function or utilizing tables computed external to the pixel shader. Accordingly, a client device, such as a multi-purpose client device that is not dedicated to image processing, may permit a user to select certain images for review and may receive, decompress and present those images in such a manner that a user may view the detailed medical images in a very computationally efficient and timely manner.

According to one aspect of the present invention, all or a portion of the system server 18 and/or client device 20 of example embodiments of the present invention generally operate under control of a computer program. The computer program for performing the methods of example embodiments of the present invention may include one or more computer-readable program code portions, such as a series of computer instructions, embodied or otherwise stored in a computer-readable storage medium, such as the non-volatile storage medium.

As described above, FIGS. 3 and 4 are flowcharts reflecting methods, systems and computer programs according to exemplary embodiments of the present invention from the perspective of the system server 18 and the client device 10, respectively. It will be understood that each block or step of the flowcharts, and combinations of blocks in the flowcharts, may be implemented by various means, such as hardware, firmware, and/or a computer program product including one or more computer program instructions. As will be appreciated, any such computer program instructions may be loaded onto a computer or other programmable apparatus to produce a machine, such that the instructions which execute on the computer or other programmable apparatus (e.g., hardware) create means for implementing the functions specified in the block(s) or step(s) of the flowcharts. These computer program instructions may also be stored in a computer-readable memory that may direct a computer or other programmable apparatus to function in a particular manner, such that the instructions stored in the computer-readable memory produce an article of manufacture including instruction means which implement the function specified in the block(s) or step(s) of the flowcharts. The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the block(s) or step(s) of the flowcharts.

Accordingly, blocks or steps of the flowcharts support combinations of means for performing the specified functions and combinations of steps for performing the specified functions. It will also be understood that one or more blocks or steps of the flowcharts, and combinations of blocks or steps in the flowcharts, may be implemented by special purpose hardware-based computer systems which perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method of normalizing Digital Imaging and Communications in Medicine (DICOM) image data comprising:
    converting, with a processor, a DICOM image to a normalized image having a different file format, wherein converting the DICOM image comprises compressing the DICOM image and converting each of a plurality of pixels of the DICOM image to a gray scale pixel format and a color pixel format;
    creating a set of related images having the different file format based upon the normalized image, wherein creating the set of related images comprises creating a plurality of images having different pixel dimensions that are all smaller than pixel dimensions of the normalized image; and
    transforming ancillary information related to the DICOM image to a human readable format.

2. A method according to claim 1 wherein converting the DICOM image to the normalized image comprises converting the DICOM image to the normalized image having a JPEG-XR format.

3. A method according to claim 1 further comprising creating an image of a sub-area extracted from the normalized image without decompressing the normalized image.

4. A method according to claim 1 further comprising creating one or more transformed images having the different file format based upon the normalized image, wherein creating the one or more transformed image comprises at least one of flipping or rotating the normalized image.

5. A method according to claim 1 further comprising creating one or more lower quality images based upon the normalized image without decompressing the normalized image.

6. A method according to claim 1 wherein transforming the ancillary information comprises storing the transformed information related to a grouping of images on a per-study basis and storing the transformed information related to a respective image in an image-specific manner.

7. A method according to claim 6 wherein transforming ancillary information related to a respective image comprises re-computing information related to image pixel values and to spatial position and orientation.

8. A method according to claim 1 further comprising providing the normalized image to a client device via web services.

9. A method according to claim 8 wherein providing the normalized image to the client device via web services comprises providing the normalized image to the client device via Representational State Transfer (REST) web services, and wherein the method further comprises providing the ancillary information in a JavaScript Object Notation (JSON) format.

10. A method according to claim 1 further comprising providing navigation information for a sequence of images in a study without providing individual image information, wherein the navigation information comprise navigational dimensions and boundaries for the navigational dimensions.

11. An apparatus for normalizing Digital Imaging and Communications in Medicine (DICOM) image data, wherein the apparatus comprises processing circuitry configured to:
   convert a DICOM image to a normalized image having a different file format by compressing the DICOM image and converting each of a plurality of pixels of the DICOM image to a gray scale pixel format and a color pixel format;
   create a set of related images having the different file format based upon the normalized image by creating a plurality of images having different pixel dimensions that are all smaller than pixel dimensions of the normalized image; and
   transform ancillary information related to the DICOM image to a human readable format.

12. An apparatus according to claim 11 wherein the processing circuitry is configured to convert the DICOM image to the normalized image by converting the DICOM image to the normalized image having a JPEG-XR format.

13. An apparatus according to claim 11 wherein the processing circuitry is further configured to create an image of a sub-area extracted from the normalized image without decompressing the normalized image.

14. An apparatus according to claim 11 wherein the processing circuitry is further configured to create one or more transformed images having the different file format based upon the normalized image, wherein the processing circuitry is configured to create the one or more transformed image by at least one of flipping or rotating the normalized image.

15. An apparatus according to claim 11 wherein the processing circuitry is configured to create one or more lower quality images based upon the normalized image without decompressing the normalized image.

16. An apparatus according to claim 11 wherein the processing circuitry is configured to transform the ancillary information by storing the transformed information related to a grouping of images on a per-study basis and storing the transformed information related to a respective image in an image-specific manner.

17. An apparatus according to claim 16 wherein the processing circuitry is configured to transform ancillary information related to a respective image by re-computing information related to image pixel values and to spatial position and orientation.

18. An apparatus according to claim 11 wherein the processing circuitry is configured to provide the normalized image to a client device via web services.

19. An apparatus according to claim 18 wherein the processing circuitry is configured to provide the normalized image to the client device via web services by providing the normalized image to the client device via Representational State Transfer (REST) web services, and wherein the processing circuitry is further configured to provide the ancillary information in a JavaScript Object Notation (JSON) format.

20. An apparatus according to claim 11 wherein the processing circuitry is configured to provide navigation information for a sequence of images in a study without providing individual image information, wherein the navigation information comprise navigational dimensions and boundaries for the navigational dimensions.

21. A computer program product for normalizing Digital Imaging and Communications in Medicine (DICOM) image data, the computer program product comprising at least one computer-readable storage medium having computer-executable program code instructions stored therein, the computer-executable program code instructions comprising program code instructions for:
   converting a DICOM image to a normalized image having a different file format, wherein converting the DICOM image comprises compressing the DICOM image and converting each of a plurality of pixels of the DICOM image to a gray scale pixel format and a color pixel format;
   creating a set of related images having the different file format based upon the normalized image, wherein creating the set of related images comprises creating a plurality of images having different pixel dimensions that are all smaller than pixel dimensions of the normalized image; and
   transforming ancillary information related to the DICOM image to a human readable format.

22. A computer program product according to claim 21 wherein computer program code instructions for converting the DICOM image to the normalized image comprise computer program code instructions for converting the DICOM image to the normalized image having a JPEG-XR format.

23. A computer program product according to claim 21 further comprising computer program code instructions for creating an image of a sub-area extracted from the normalized image without decompressing the normalized image.

24. A computer program product according to claim 21 further comprising computer program code instructions for creating one or more transformed images having the different file format based upon the normalized image, wherein the computer program code instructions for creating the one or more transformed image comprise computer program code instructions for at least one of flipping or rotating the normalized image.

25. A computer program product according to claim 21 further comprising computer program code instructions for creating one or more lower quality images based upon the normalized image without decompressing the normalized image.

26. A computer program product according to claim 21 wherein the computer program code instructions for transforming the ancillary information comprise computer program code instructions for storing the transformed information related to a grouping of images on a per-study basis and computer program code instructions for storing the transformed information related to a respective image in an image-specific manner.

27. A computer program product according to claim 26 wherein the computer program code instructions for transforming ancillary information related to a respective image comprise computer program code instructions for re-computing information related to image pixel values and to spatial position and orientation.

28. A computer program product according to claim 21 further comprising computer program code instructions for providing the normalized image to a client device via web services.

29. A computer program product according to claim 28 wherein the computer program code instructions for providing the normalized image to the client device via web services comprise computer program code instructions for providing the normalized image to the client device via Representational State Transfer (REST) web services, and wherein the computer program product further comprises computer program code instructions for providing the ancillary information in a JavaScript Object Notation (JSON) format.

30. A computer program product according to claim 1 further comprising computer program code instructions for providing navigation information for a sequence of images in a study without providing individual image information, wherein the navigation information comprise navigational dimensions and boundaries for the navigational dimensions.

* * * * *

UNITED STATES PATENT AND TRADEMARK OFFICE
CERTIFICATE OF CORRECTION

PATENT NO. : 8,417,043 B2
APPLICATION NO. : 13/075495
DATED : April 9, 2013
INVENTOR(S) : Bocirnea It is certified that error appears in the above-identified patent and that said Letters Patent is hereby corrected as shown below:

In the Specifications:

Column 9,
Lines 46 and 47 should appear as follows:
"be defined as $\{I_1 \ldots I_n; D_n = \{X/(2_n), Y/(2_n)\}$ and $(X/2_n \geq 2_k$ or $Y/2_n \geq 2_k)\}$. In this representation, the maximum dimension of"

Signed and Sealed this
Twenty-seventh Day of August, 2013

Teresa Stanek Rea
*Acting Director of the United States Patent and Trademark Office*